US00PP28644P2

(12) United States Plant Patent
van Sambeek

(10) Patent No.: US PP28,644 P2
(45) Date of Patent: Nov. 14, 2017

(54) ***PHLOX* PLANT NAMED 'BARPHEARCER'**

(50) Latin Name: *Phlox paniculata*
Varietal Denomination: Barphearcer

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,228

(22) Filed: Aug. 27, 2016

(51) Int. Cl.
*A01H 5/02* (2006.01)

(52) U.S. Cl.
USPC ..... Plt./320

(58) Field of Classification Search
USPC ..... Plt./320
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phlox* plant named 'Barphearcer', characterized by its upright and mounding plant habit; vigorous growth habit; early and freely flowering habit; purple violet-colored flowers; and good garden performance.

1 Drawing Sheet

Botanical designation: *Phlox paniculata.*
Cultivar denomination: 'BARPHEARCER'.

BACKGROUND OF THE INVENTION

The present invention relates to a new and distinct cultivar of *Phlox* plant, botanically known as *Phlox paniculata* and hereinafter referred to by the name 'Barphearcer'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from a cross-pollination made by the Inventor in July, 2011 in Aalsmeer, The Netherlands, of a proprietary selection of *Phlox paniculata* identified as code number PA-09-000003-02, not patented, as the female, or seed, parent with a proprietary selection of *Phlox paniculata* identified as code number PA0049, not patented, as the male, or pollen, parent. The new *Phlox* plant was discovered and selected by the Inventor as a single flowering plant from within the progeny of the stated cross-pollination in a controlled environment in Aalsmeer, The Netherlands in July, 2012.

Asexual reproduction of the new *Phlox* plant by cuttings in a controlled environment in Aalsmeer, The Netherlands since March, 2013 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barphearcer'. These characteristics in combination distinguish 'Barphearcer' as a new and distinct *Phlox* plant:

1. Upright and mounding plant habit.
2. Vigorous growth habit.
3. Early and freely flowering habit.
4. Purple violet-colored flowers.
5. Good garden performance.

Plants of the new *Phlox* differ primarily from plants of the female parent selection in flower color as plants of the female parent selection have red-colored flowers.

Plants of the new *Phlox* differ primarily from plants of the male parent selection in the following characteristics:

1. Plants of the new *Phlox* flower earlier than plants of the male parent selection.
2. Plants of the new *Phlox* and the male parent selection differ in flower color as flowers of plants of the male parent selection have pink-colored centers.
3. Plants of the new *Phlox* are more low temperature-tolerant than plants of the male parent selection.

Plants of the new *Phlox* can be compared to plants of *Phlox paniculata* 'Sweet Summer', not patented. In side-by-side comparisons, plants of the new *Phlox* and 'Sweet Summer' differ in the following characteristics:

1. Plants of the new *Phlox* are more compact than plants of 'Sweet Summer'.
2. Plants of the new *Phlox* have smaller leaves than plants of 'Sweet Summer'.
3. Plants of the new *Phlox* are more freely flowering than plants of 'Sweet Summer'.
4. Plants of the new *Phlox* flower two weeks earlier than plants of 'Sweet Summer'.
5. Plants of the new *Phlox* have smaller inflorescences and smaller flowers than plants of 'Sweet Summer'.
6. Plants of the new *Phlox* and 'Sweet Summer' differ in flower color as plants of 'Sweet Summer' have white-colored flowers.
7. Plants of the new *Phlox* are more low temperature tolerant than plants of 'Sweet Summer'.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Barphearcer' grown in a container.

DETAILED BOTANICAL DESCRIPTION

The aforementioned photograph and following observations, measurements and values describe plants grown during the spring and early summer in 13-cm containers in a glass-covered greenhouse in Aalsmeer, The Netherlands and under cultural practices typical of commercial *Phlox* production. During the production of the plants, day temperatures averaged 21° C. and night temperatures averaged 15° C. Plants were pinched one time and were three months old when the photograph was taken and 14 months old when the description was taken. In the following description, color references are made to The Royal Horticultural Society Colour Chart, 2001 Edition, except where general terms of ordinary dictionary significance are used.

Botanical classification: *Phlox paniculata* 'Barphearcer'.

Parentage:

*Female, or seed, parent*.—Proprietary selection of *Phlox paniculata* identified as code number PA-09-000003-002, not patented.

*Male, or pollen, parent*.—Proprietary selection of *Phlox paniculata* identified as code number PA-0049, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and mounding plant habit; vigorous growth habit.

*Plant height*.—About 35 cm.

*Plant width* (*spread*).—About 30 cm.

*Lateral branches*.—Length: About 35 cm. Internode length: About 2 cm. Strength: Strong. Aspect: Mostly upright. Texture: Sparsely pubescent. Color: Close to 79A.

Leaf description:

*Arrangement*.—Opposite, simple.

*Length*.—About 7 cm.

*Width*.—About 2.5 cm.

*Shape*.—Ovate to elliptic.

*Apex*.—Acute.

*Base*.—Attenuate.

*Margin*.—Entire, ciliate.

*Texture, upper and lower surfaces*.—Pubescent.

*Venation pattern*.—Pinnate, reticulate.

*Color*.—Developing leaves, upper surface: Close to 141A. Developing leaves, lower surface: Close to 138A. Fully expanded leaves, upper surface: Close to 137A; venation, close to 144D. Fully expanded leaves, lower surface: Close to 147B; venation, close to 144D.

*Petioles*.—Length: About 2 mm. Diameter: About 2 mm. Texture, upper and lower surfaces: Smooth, glabrous. Color, upper and lower surfaces: Close to 144D.

Flower description:

*Flower type and flowering habit*.—Single rotate and salverform flowers arranged in compound terminal and lateral panicles; flowers face mostly upright; freely flowering habit with about 40 to 50 flowers per inflorescence and about 600 flowers developing per plant during the flowering season.

*Fragrance*.—Slightly fragrant, pleasant.

*Natural flowering season*.—Early flowering habit, plants begin flowering about ten to eleven weeks after planting; plants flower naturally during July in The Netherlands; flowers persistent.

*Flower buds*.—Height: About 1.3 cm. Diameter: About 3 mm. Shape: Ovoid. Color: Close to 155A.

*Inflorescence height*.—About 12 cm.

*Inflorescence diameter*.—About 13 cm.

*Flower diameter*.—About 2.4 cm.

*Flower depth*.—About 2 cm.

*Flower throat diameter*.—About 2.5 mm.

*Flower tube length*.—About 1.9 cm.

*Flower diameter, proximally*.—About 2 mm.

*Petals*.—Quantity per flower: Typically five in a single whorl; petals fused at the base into a narrow tube. Lobe length: About 1.1 cm. Lobe width: About 1 cm. Lobe shape: Rounded. Lobe apex: Obtuse. Lobe margin: Entire. Lobe texture, upper and lower surfaces: Smooth, glabrous. Throat texture: Mostly smooth, glabrous; at the base, pubescent. Tube texture: Pubescent. Color: When opening and fully opened, upper surface: Close to 80A; towards the throat, close to 74A; venation, close to 80A. When opening and fully opened, lower surface: Close to 82B; venation, close to 82B. Throat: Close to 82A; venation, close to 82A. Tube: Close to 77A; venation, close to 77A.

*Sepals*.—Quantity per flower: Typically five in a single whorl, fused towards the base; calyx, campanulate. Length: About 9 mm. Width: About 1 mm. Shape: Narrowly deltoid. Apex: Acuminate. Margin: Entire. Texture, upper surface: Smooth, glabrous. Texture, lower surface: Pubescent. Color: When opening and fully opened, upper surface: Close to 137B. When opening and fully opened, lower surface: Close to 137C.

*Peduncles*.—Length: About 7 cm. Diameter: About 1.5 mm. Strength: Moderately strong. Texture: Smooth, glabrous. Color: Close to 144A.

*Pedicels*.—Length: About 1 cm. Diameter: About 0.5 mm. Strength: Moderately strong. Texture: Pubescent. Color: Close to 144A.

*Reproductive organs*.—Stamens: Quantity per flower: Typically five. Filament length: About 2 mm. Filament color: Close to 155C. Anther length: About 1 mm. Anther color: Close to 8C. Pollen amount: None observed. Pistils: Quantity per flower: One. Pistil length: About 1.9 cm. Stigma shape: Cleft, three-parted. Stigma color: Close to 8C. Style length: About 1.7 cm. Style color: Close to 144D. Ovary color: Close to 144A.

*Seeds and fruits*.—Seed and fruit development have not been observed on plants of the new *Phlox*.

Garden performance: Plants of the new *Phlox* have been observed to have good garden performance and tolerate rain, wind and frost.

Disease & pest resistance: Plants of the new *Phlox* have not been observed to be resistant to pathogens and pests common to *Phlox* plants.

It is claimed:

1. A new and distinct *Phlox* plant named 'Barphearcer' as illustrated and described.

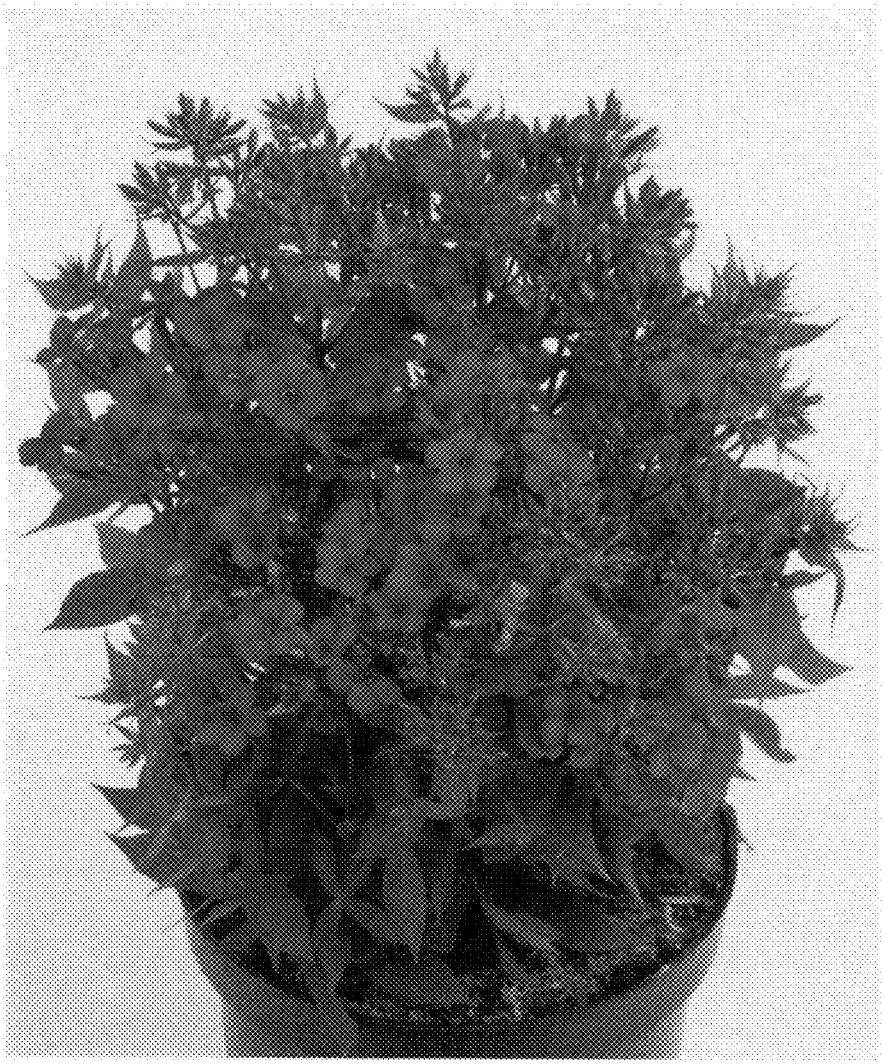

* * * * *